US009775509B2

(12) United States Patent
Fung et al.

(10) Patent No.: US 9,775,509 B2
(45) Date of Patent: Oct. 3, 2017

(54) AUTOMATIC OPTOMETRY ANALYSIS SYSTEM FOR CHILDREN (71) Applicant: Hong Kong Fortune Technology Limited, Hong Kong (HK)

(72) Inventors: Dan Lai Fung, Hong Kong (HK); Zhi Sheng Li, Hong Kong (HK); Geng Li, Hong Kong (HK)

(73) Assignee: Hong Kong Fortune Technology Limited, Hong Kong (HK)

( * ) Notice: Subject to any disclaimer, the term of this patent is extended or adjusted under 35 U.S.C. 154(b) by 0 days.

(21) Appl. No.: 15/190,228

(22) Filed: Jun. 23, 2016

(65) Prior Publication Data

US 2017/0027434 A1   Feb. 2, 2017

Related U.S. Application Data (60) Provisional application No. 62/197,523, filed on Jul. 27, 2015.

(30) Foreign Application Priority Data

May 4, 2016  (CN) .......................... 2016 1 0288359

(51) Int. Cl.
*A61B 3/10*      (2006.01)
*A61B 3/00*      (2006.01)
(Continued)

(52) U.S. Cl.
CPC .......... *A61B 3/0025* (2013.01); *A61B 3/0041* (2013.01); *A61B 3/0091* (2013.01);
(Continued)

(58) Field of Classification Search
CPC ......... A61B 3/028; A61B 3/103; A61B 3/032; A61B 3/0041; A61B 3/0091; A61B 2503/06; G05B 2219/21109
(Continued)

(56) References Cited

U.S. PATENT DOCUMENTS 2,322,878 A  *  6/1943  Peck .................... A61B 3/04
                                                         351/235
5,892,567 A  *  4/1999  Hosoi .................. A61B 3/0285
                                                         351/205

(Continued)

FOREIGN PATENT DOCUMENTS

ES   WO 2013126410 A1  *  8/2013  ............. A61B 3/028

OTHER PUBLICATIONS

STIC search Feb. 14, 2014.*
(Continued)

*Primary Examiner* — Stephone B Allen
*Assistant Examiner* — Travis Fissel (57) ABSTRACT The automatic optometry analysis system for children includes a main control board for obtaining optometry data of a patient, and an upper computer connected with the main control board. The upper computer may carry out processing according to the optometry data obtained from the main control board, generate corresponding preliminary eyeglass prescription data, correct the preliminary eyeglass prescription data based on collected preset patient information, and generate a final eyeglass prescription suitable for the patient; wherein correction of the preliminary eyeglass prescription data based on the collected preset patient information includes the use of age-related correction coefficient to correct the preliminary eyeglass prescription data.

18 Claims, 5 Drawing Sheets

(51) Int. Cl.
*A61B 3/028* (2006.01)
*A61B 3/032* (2006.01)
*A61B 3/103* (2006.01)
*G06F 19/00* (2011.01)
*G05B 19/042* (2006.01)

(52) U.S. Cl.
CPC .............. *A61B 3/028* (2013.01); *A61B 3/032* (2013.01); *A61B 3/103* (2013.01); *G05B 19/042* (2013.01); *G06F 19/345* (2013.01); *G06F 19/3443* (2013.01); *A61B 2503/06* (2013.01); *G05B 2219/21109* (2013.01); *G06F 19/3487* (2013.01)

(58) Field of Classification Search
USPC ........ 351/200–202, 204–221, 224–226, 237, 351/238, 243, 246
See application file for complete search history.

(56) References Cited

U.S. PATENT DOCUMENTS

| | | | |
|---|---|---|---|
| 8,820,931 B2* | 9/2014 | Walsh | A61B 3/102 351/206 |
| 2002/0019749 A1* | 2/2002 | Becker | G06F 19/325 705/2 |
| 2011/0075097 A1* | 3/2011 | Hamaguchi | A61B 3/12 351/211 |

OTHER PUBLICATIONS https://web.archive.org/web/20131109191909/http://www.allaboutvision.com/eyeglasses/eyeglass-prescription.htm.*
European Search Report of counterpart European Patent Application No. 16175800.8 dated Dec. 6, 2016.

* cited by examiner

Patient Female 13 years old

|  |  | Spherical lens | Cylindrical lens | Axis |
|---|---|---|---|---|
| Power before pupillary dilation is | OD | -11.00DS | =-0.50DC | X 135 |
|  | OS | -3.50DS | =-1.00DC | X 90 |
| Power after pupillary dilation is | OD | -10.00DS |  |  |
|  | OS | -3.25DS | =-1.00DC | X 90 |
| Power of eyeglass prescription 1 is | OD | -9.50DS |  |  |
|  | OS | -3.50DS | =-0.75DC | X 90 |
| Power of eyeglass prescription 2 is | OD | -9.00DS |  |  |
|  | OS | -3.50DS | =-0.75DC | X 90 |

Spherical lens result of eyeglass prescriptions 1 and 2
Eyeglass prescription spherical lens power= Spherical lens power after pupillary dilation - f coefficient Cylindrical lens result of eyeglass prescriptions 1 and 2
Eyeglass prescription cylindrical lens power= Cylindrical lens power after pupillary dilation - f coefficient Axis result of eyeglass prescription
Axis value of eyeglass prescription= Axis value after pupillary dilation

Fig. 8

Patient Female 10 years old

|  |  | Spherical lens | Cylindrical lens | Axis |
|---|---|---|---|---|
| Power before pupillary dilation is | OD | +6.00DS | =+1.25DC | X 70 |
|  | OS | +1.00DS | =+1.00DC | X 85 |
| Power after pupillary dilation is | OD | +7.50DS | =+1.00DC | X 70 |
|  | OS | +2.00DS | =+1.00DC | X 90 |
| Power of eyeglass prescription 1 is | OD | +5.00DS | =+0.50DC | X 70 |
|  | OS | +2.00DS | =+0.50DC | X 90 |
| Power of eyeglass prescription 2 is | OD | +5.50DS | =+0.50DC | X 70 |
|  | OS | +2.00DS | =+0.50DC | X 90 |

Spherical lens result of eyeglass prescriptions 1 and 2
Eyeglass prescription spherical lens power= Spherical lens power after pupillary dilation - f coefficient Cylindrical lens result of eyeglass prescriptions 1 and 2
Eyeglass prescription cylindrical lens power= Cylindrical lens power after pupillary dilation - f coefficient Axis result of eyeglass prescription
Axis value of eyeglass prescription= Axis value after pupillary dilation

Fig. 9

AUTOMATIC OPTOMETRY ANALYSIS SYSTEM FOR CHILDREN

CROSS-REFERENCE TO RELATED APPLICATIONS

The present application claims the benefit of U.S. Provisional Patent Application No. 62/197,523 filed Jul. 27, 2015 and Chinese Patent Application No. 201610288359.2 filed on May 4, 2016, the entire content of which is hereby incorporated by reference.

FIELD OF THE TECHNOLOGY

The present application relates to eye refraction correction for children, and particularly to an automatic optometry analysis system for children.

BACKGROUND

With the development of medical technology, optometry machines aiming at ophthalmology have been rapidly developed. At present, refractometers have been widely used in the world. This greatly facilitates people's need for optometry. However, the difference in skill level of operators of optometry machines, the effect of coordination of patients, and the difference in adjustment ability of individuals would lead to divergence and uncertainty of the optometry results. Relying on these inaccurate optometry results would have many adverse effects on patients' eye refraction correction. It could cause fatal eye damage especially to children during eye development period. If optometrists of inferior skill provide children with eyeglasses with inappropriate prescription, it will make eye vision worse. Clinical reports show a large number of cases resulting in poorer vision due to inappropriate prescription. Famous ophthalmology hospital also have such problems. There are only a handful of experienced children ophthalmologist. Effective diagnosis and prescription for children with ametropia is an important issue in the field of ophthalmology for children.

Specifically, when a patient with ametropia undergoes physical correction for eyeglass prescription, an optometrist would come up with an eyeglass prescription for nearsightedness and farsightedness through optometry instrument for reference, and then produce a suitable pair of eyeglasses through a try-out period. The suitability of the eyeglasses depends on the ability of the optometrist, the cognitive level of the patients, and coordination of patients. There exists divergence and uncertainty of the result. Since the eyes of adult have fully developed, it will not cause too much damage to the eyes even though eyeglasses and eye condition are not consistent. However, when this optometry process is aimed at teenagers, especially children, the result is not the same because the eyes of children are in development stage. If the potential refraction adjustment of the eyes of children is not taken into consideration, and eyeglass prescription is given only according to the optometry machine, it may damage eye development of children, inhibit the full play of eye adjustment, result in loss of eye plasticity, and lead to unrecoverable of vision.

Targeted eyeglass prescription can make many patients with false abnormal eye refraction recover to normal vision. This relies on exquisite technique of children eye doctors. However, there is a lack of eye doctors who can systematically handle this technology. Thus, there is a need to solve the problem technologically so that patients do not have to rely on the experience of children's eye doctors, and can conveniently and accurately give targeted eyeglass prescription to patients especially for children with ametropia.

SUMMARY

According to one aspect, there is provided an automatic optometry analysis system for children, including a main control board for obtaining optometry data of a patient, and an upper computer connected with the main control board; wherein the upper computer carries out processing according to the optometry data obtained from the main control board, generates a corresponding preliminary eyeglass prescription data, corrects the preliminary eyeglass prescription data based on collected preset patient information, and generates a final eyeglass prescription suitable for the patient; and wherein correction of the preliminary eyeglass prescription data based on the collected preset patient information includes the use of age-related correction coefficient to correct the preliminary eyeglass prescription data.

In one embodiment, the main control board uses a field-programmable gate array (FPGA) unit as a central processing core; wherein the FPGA unit is connected with a USB interface through a USB interface control unit and connected with the upper computer through the USB interface, and the FPGA unit is connected with an optical system through an IO interface and connected with a motion platform with a 3-axis motor through an optoelectronic isolator; and wherein the motion platform is further connected with a motor drive unit, and the FPGA unit and the motor drive unit are both connected with a level conversion unit.

In one embodiment, the FPGA unit is an EP3C16Q240C8N chip, the motor drive unit is a SLA7042M driver chip for special use in a 2-phase motor, the level conversion unit is a 16-bit 3.3V-5V SN74ALVC164245 level conversion chip, and the USB interface control unit is a PDIUSBD12 chip.

In one embodiment, the FPGA unit includes:
a USB interface control module as a FPGA internal USB firmware program for implementing communication between the FPGA unit and the USB interface of the upper computer;
a clock module for carrying out frequency division and multiplication processes on an external clock, and generating clock signals of various frequencies required by operation of the FPGA unit;
a command analysis module for analyzing command received from the upper computer, generating an executive order according to a stipulated command protocol, and sending the executive order to a corresponding module for execution;
a motor control module for executing a 3-axis motor control command sent from the command analysis module, and carrying out subdivision and variable speed control of the motor of each axis, and eventually implementing 3-axis linkage control through transmission of different commands to the motor drive unit; and
a light source control module for controlling an LED infrared light source and a visual aid light source of the optical system, the visual aid light source being used to guide eye-glazing direction of the patient, and the LED infrared light source being used to aid in focusing.

In one embodiment, in the eyeglass prescription, spherical lens power=spherical lens power after pupillary dilation−f1 coefficient, wherein the f1 coefficient possesses age correlation and correlation of spherical lens after pupillary dilation; cylindrical lens power=cylindrical lens power after pupillary dilation−f2 coefficient, wherein the f2 coefficient possesses age correlation and correlation of cylindrical lens after pupillary dilation; and axis=axis after pupillary dilation.

In one embodiment, the eyeglass prescription is generated based on an expert database on children optometry of children, wherein the expert database includes a huge volume of optometry data from youngsters and children aged 3-18 formed by carrying out statistical analysis of successful eyeglass prescription cases of experts using database building language and C language so as to establish an associated database model; and wherein the automatic optometry analysis system for children displays or prints out two sets of eyeglass prescription based on recognition of patients' age, small pupil power and large pupil power.

In one embodiment, ages of patients are divided into a predetermined number of age groups, and a correction coefficient corresponds to each age group in the eyeglass prescription such that eyeglass prescription power given in the eyeglass prescription increases as the age group increases; wherein in the eyeglass prescription, refraction condition of the patient after pupillary dilation is set as a primary reference factor, and refraction condition of the patient before pupillary dilation is set as a secondary reference factor.

In one embodiment, the refraction condition includes farsightedness, in an eyeglass prescription, both spherical lens and cylindrical lens can be null, if the cylindrical lens is null, axis is null, astigmatic axis is marked by 1-180; in an eyeglass prescription result, spherical lens and cylindrical lens are positive numbers, minimum value is blank and is considered as zero; large pupil spherical lens must be larger than small pupil spherical lens; large pupil spherical lens is +0.25 DS to +15.00 DS, large pupil cylindrical lens is +0.25 DC to +8.25 DC; and one large pupil cylindrical lens corresponds to five small pupil cylindrical lenses.

In one embodiment, the refraction condition includes nearsightedness, in an eyeglass prescription, both spherical lens and cylindrical lens can be null, if the cylindrical lens is null, axis does not exist; if large pupil spherical lens is null, its corresponding small pupil spherical lens power is larger than or equal to the absolute value of −0.25 DS; absolute value of large pupil spherical lens power is absolutely smaller than absolute value of small pupil spherical lens power; axis is a positive integer from 1-180 without decimal point; large pupil spherical lens is −0.25 DS to −15.00 DS, incrementing in order by a unit of 0.25, large pupil cylindrical lens is −0.25 DC to −7.00 DC, axis is set as an input value; and large pupil, small pupil and eyeglass prescription axes are consistent.

BRIEF DESCRIPTION OF THE DRAWINGS

FIG. 8 is an example of a nearsightedness prescription of the automatic optometry analysis system for children according to an embodiment of the present application.

FIG. 9 is an example of a farsightedness prescription of the automatic optometry analysis system for children according to an embodiment of the present application.

DETAILED DESCRIPTION

The automatic optometry analysis system for children of the present application is suitable for patients with ametropia, and especially suitable for youngsters and children. It combines data from successful cases of treatment of ametropia by ophthalmologist, forms a common rule for children with ametropia, and solves the problems of collecting, storing, organizing, sharing and utilizing of multi-source heterogeneous data. It provides a technical means for an effective norm for optometry of children with ametropia, and enhance the accuracy and efficiency of optometry of children with ametropia.

Figure 1:
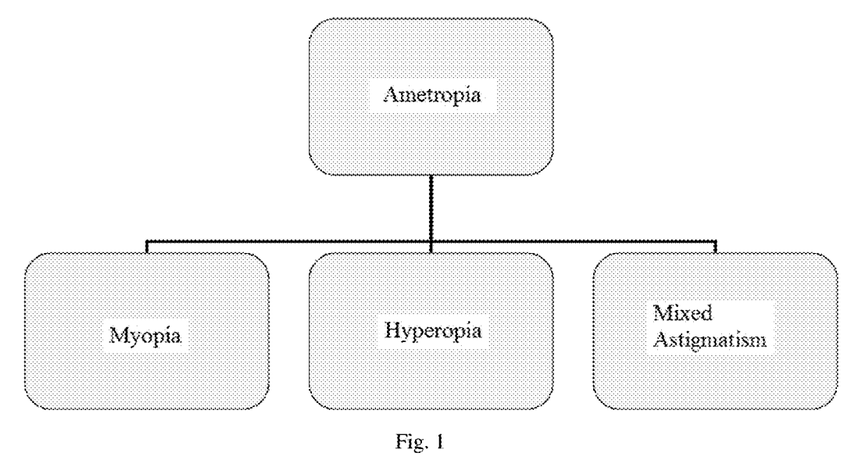
FIG. 1 shows a classification of ametropia.

In the present application, ametropic classification, ages of patients, etc. are considered. The factors to be considered are basically classified as follows:

Ametropia conditions are divided into nearsightedness, farsightedness and mixed astigmatism (see FIG. 1)

Age interval of patients is 1-18 years old (preset information on ages of patients can be collected)

Each condition includes four blocks: refractive condition after dropping of eye drop (after pupillary dilation), refractive condition before dropping of eye drop (before pupillary dilation), eyeglass prescription 1, eyeglass prescription 2

Each block is a combination of three parts, namely spherical lens, cylindrical lens and axis.

During eyeglass prescription, it has the following age correlation:

Age is divided into six groups, namely 1-3, 4-6, 7-9, 10-12, 13-15 and 16-18 years old power provided by eyeglass prescription increases as age group increases Regarding refractive condition correlation after pupillary dilation, it needs to consider:

refraction condition of a patient after pupillary dilation as a primary reference factor in an eyeglass prescription refraction condition of a patient before pupillary dilation as a secondary reference factor in an eyeglass prescription In an eyeglass prescription, spherical lens power=spherical lens power after pupillary dilation (as preliminary eyeglass prescription data)−f1 coefficient (f1 coefficient is spherical lens correction coefficient, and possesses age correlation+correlation of spherical lens after pupillary dilation)

Unit of spherical lens is "DS"

In an eyeglass prescription, cylindrical lens power=cylindrical lens power after pupillary dilation (as preliminary eyeglass prescription data)−f2 coefficient (f2 coefficient is a cylindrical lens correction coefficient, and possesses age correlation and correlation of cylindrical lens power after pupillary dilation)

Unit of cylindrical lens is "DC"

Axis of eyeglass prescription=axis after pupillary dilation

Axis has no unit

Based on the above considerations, if children optometric technology is formed into a product, a large number of children's eye doctors can easily learn how to master the technology, then the technical services provided by eye doctors will be of expert level. It can serve a large number of children with ametropia. It is no doubt beneficial to many people and has significant meaning. Based on the above idea, the present application provides an automatic optometry analysis system for children. Suitable eyeglass prescriptions are produced through integration of medical cases of children ophthalmologists and examples of cases, and according to the ages, refraction accommodation capability of patients, through collection and retrieval of information.

Patients can share high quality diagnostic services at expert level even though the eye doctors contacted are not experts.

The automatic optometry analysis system for children of the present embodiment is a diagnostic equipment established on the basis of a database of expert cases. The database of expert cases is an accumulation of experience for nearly 30 years of clinical practice of children ophthalmologists, including statistics and summary of successful cases of treatment of 100,000 children with ametropia. It is proven to be effective. Nevertheless, the formation of such a database is a technical issue because the recording, summarizing, analyzing and refining of data, and the coverage of myopia, hyperopia, astigmatism, ages of children, refraction regulating and many other factors present a challenge for the establishment of a database model. The automatic optometry analysis system for children of the embodiment in the present application contains and utilizes the database of expert cases.

Figure 2:
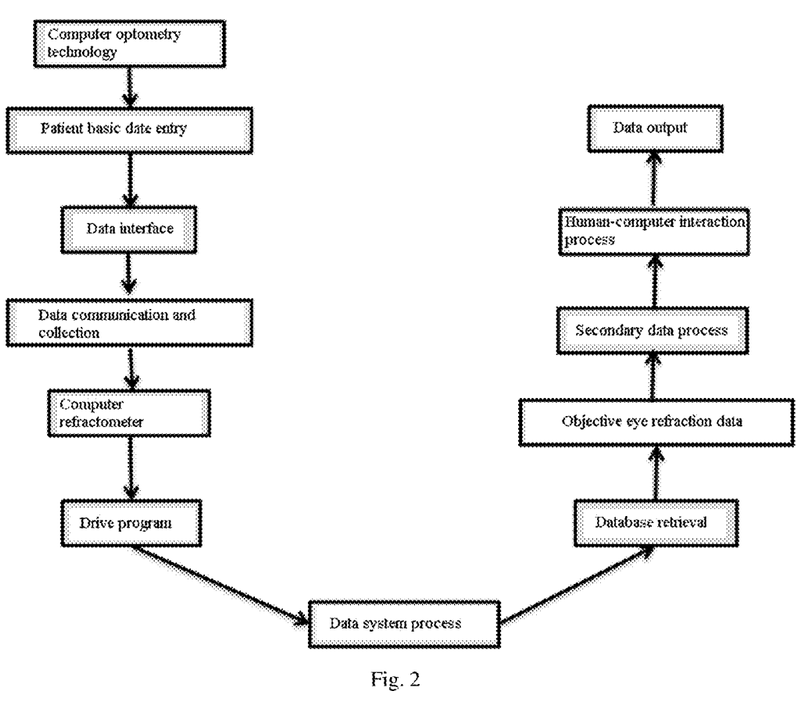
FIG. 2 is a flow chart of an automatic optometry analysis system for children according to an embodiment of the present application.
Figure 3:
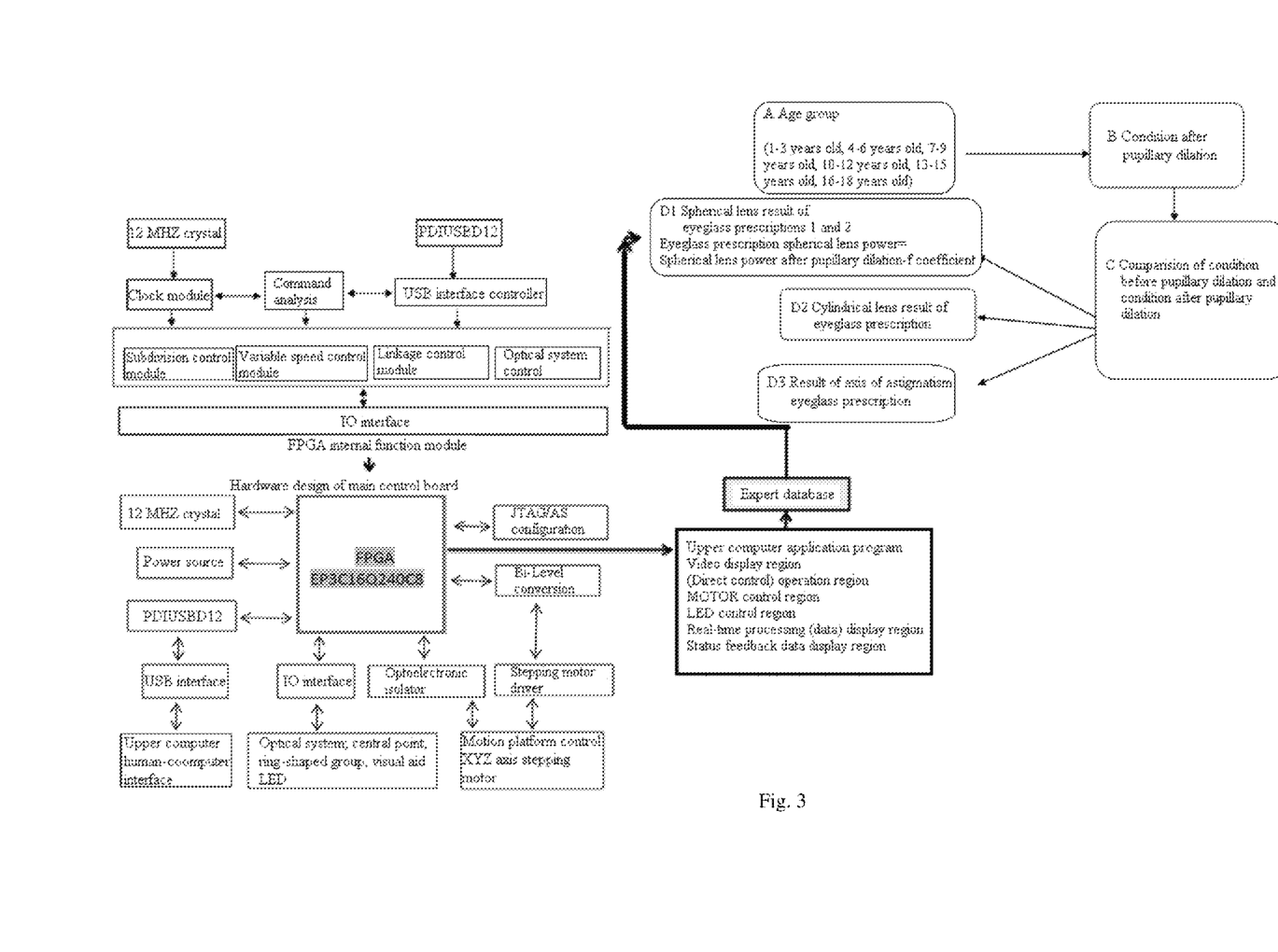
FIG. 3 is a structural diagram of the automatic optometry analysis system for children according to an embodiment of the present application.

Referring to FIG. 2, the automatic optometry analysis system for children of the present application makes use of matured optometric technology, obtains objective eye refraction data, and carries out secondary data processing according to database of expert cases. It involves technical aspects such as communication, collection, process and output of data. On the basis of a conventional refractometer, the automatic optometry analysis system for children of the embodiment of the present application may further include data interfaces and drivers, complete technical design of database retrieval, basic data entry, and human-computer interaction. It involves technical contents such as the design of DSP (digital system processor) application program in the field of computer application and the design of software and hardware interfaces. Its basic structure is shown in FIG. 3.

For software, the automatic optometry analysis system for children of the present application is based on optometry and medical schemes of children ophthalmologists to form database systems of practical medical cases and interactive index communication software. For hardware, the system mainly uses refractometers, desktop computers, and printers, etc. to form the automatic optometry analysis system for children of the present application. The automatic optometry analysis system for children of the present application mainly includes a main control board for obtaining optometry data of a patient, and an upper computer can be connected with the main control board. The upper computer may carry out processing according to the optometry data obtained from the main control board, generate corresponding preliminary eyeglass prescription data, correct the preliminary eyeglass prescription data based on collected predetermined patient information, and generate a final eyeglass prescription suitable for the patient; wherein correction of the preliminary eyeglass prescription data based on the collected predetermined patient information comprises the use of age-related correction coefficient to correct the preliminary eyeglass prescription data.

The main functions of the automatic optometry analysis system for children of an embodiment of the present application include:

a) possess subjective eye refraction optometric function;

b) display or print out two sets of eyeglass prescriptions after recognition of children's age, small pupil power and large pupil power.

The main technical standards of the automatic optometry analysis system for children of an embodiment of the present application include:

a) Apex distance: 0.0, 12.0, 13.75;

b) Spherical lens: −20.00~+20.00D (when VD=12 mm);

c) (Step: 0.12D): 0.12D, 0.25D;

d) Cylindrical lens: 0.00~±8.00D (step: 0.12D);

e) Axial: 1~180° (step: 1°);

f) Astigmatism mark: −, +, ±;

g) Pupillary distance: 45~75 mm;

h) Minimum detectable pupil: 2.5 mm;

i) Data storage: retention of data of 3 times measurement using one eye;

j) Internal printer: thermal sensitive line printer;

k) Power source: 220V±10% 50 Hz.

The automatic optometry analysis system for children of the present application utilizes design scheme of refractometer control system of FPGA (field-programmable gate array) and USB interface. The interface design of computerized optometry in the design scheme can be a modification based on a conventional refractometer. A computer control system can be designed based on FPGA. It can also utilize USB technology to connect devices with the computer, and increase the speed of data transmission. An eyeglass prescription for children can be obtained from interaction with the expert database through a computer keyboard.

Figure 4:
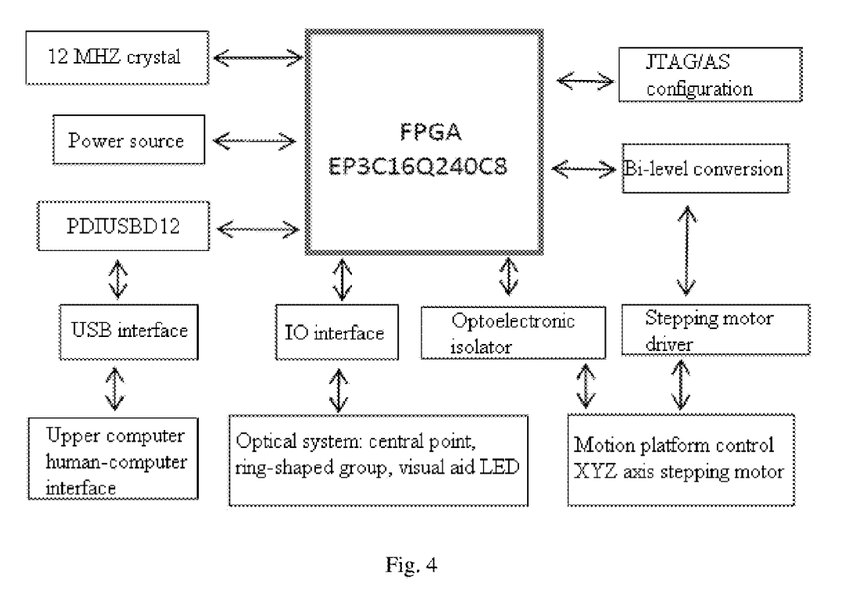
FIG. 4 is a block diagram of the design of hardware of a main control board of the automatic optometry analysis system for children according to an embodiment of the present application.

The control system is the core of the control of the automatic optometry analysis system for children. It does not only realize movement and light source control of multi-axis motors, it also realizes the exchange of information of the upper computer and other important functions. The design of the main control board of the automatic optometry analysis system for children of the present application can be an expansion of the smallest EP3C16Q240C8 system. It can carry out appropriate modification of pin interface based on FPGA function realization and related external expansion. It may also have the addition of a USB communication interface, a motor driving module, and an optoelectronic isolator circuit of travel switch signal. FIG. 4 shows a block diagram of the design of hardware of a main control board of the automatic optometry analysis system for children.

In FIG. 4, the FPGA on the main control board is an EP3C16Q240C8N chip of the Cylone III system manufactured by Altera Company. The chip has 15,408 logical units. It can provide a random-access memory (RAM) of 516,096 bytes. The chip may also carry 4 phase-locked loops. It can ensure steadiness when the clock signal of the system operates in high speed. A 12MHz crystal can be used for clock signal of the system. The motor drive unit can be a SLA7042M driver chip for special use in a 2-phase motor manufactured by Allergo Company. It can achieve a super smooth and low speed drive. In order to realize communication between the main chip and the external equipment, the control board requires conversion of 3.3V and 5V levels.

The FPGA may utilize a 16-bit 3.3V-5V level conversion SN74ALVC164245 chip manufactured by TI Company. The USB interface control unit can be a PDIUSBD12 chip. It is an integration of SIE FIFO read-only memory, transceiver and voltage regulator suitable for certain external equipment. As a central processor of the entire main control board, the FPGA unit connects with a bi-level conversion unit and a USB interface control unit respectively. The USB interface control unit can be connected with the USB interface, connected with the upper computer through the USB interface, and interacted with the FPGA unit through the human-computer interface of the upper computer. The bi-level conversion unit may also connect with the motor drive unit. The motor drive unit may connect with the motion platform, and control the 3-axis (XYZ) motor. At the same time, the FPGA unit may connect with the motion platform through the optoelectronic isolator. The FPGA unit may also connect with the optical system through IO interface.

Figure 5:
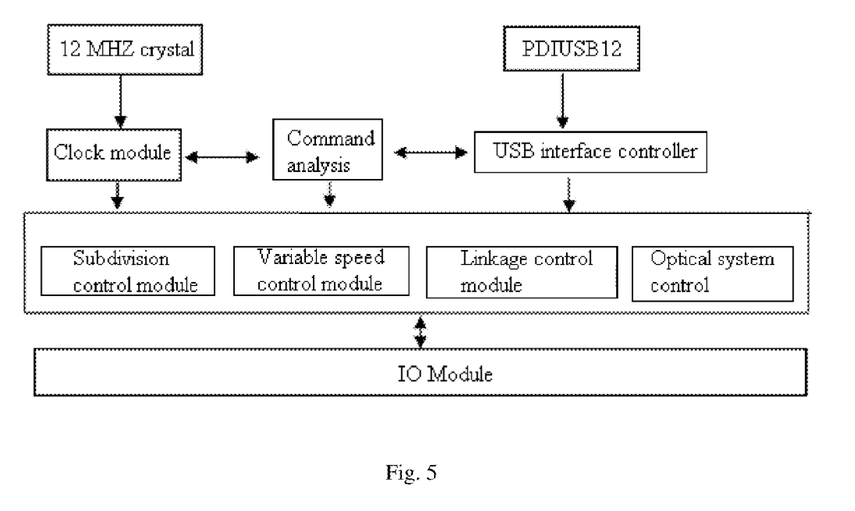
FIG. 5 is a block diagram of the internal functional modules of the FPGA of the automatic optometry analysis system for children according to an embodiment of the present application.
Figure 6:
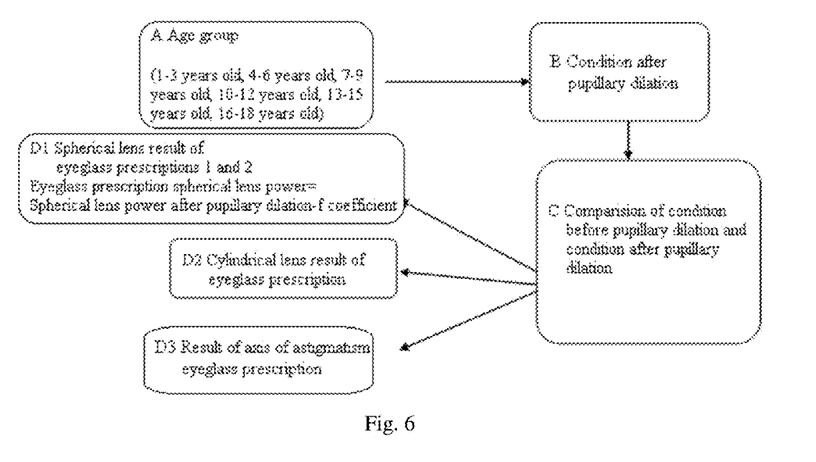
FIG. 6 is a flowchart of eyeglass prescription of the automatic optometry analysis system for children according to an embodiment of the present application.
Figure 7:
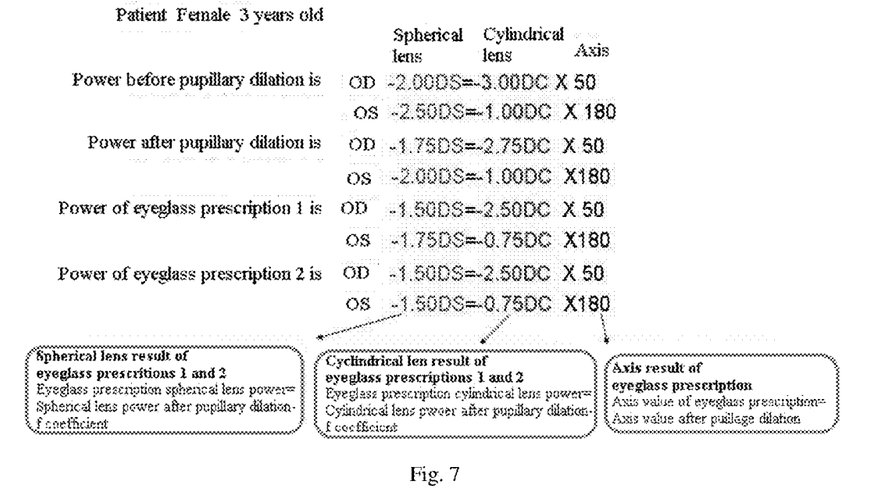
FIG. 7 is a composition formula of nearsightedness, farsightedness and mixed astigmatism used in the automatic optometry analysis system for children according to an embodiment of the present application.

Verilog HDL is a hardware description language. It is mainly used for digital system modeling of various abstract design levels from algorithm level, gate level to switch level. The FPGA chip is the core element of the main control board of the refractometer. In the present design scheme, Verilg HDL may be used in the FPGA in order to realize the exchange of information between the upper and lower computers, the control of the multi-axis linkage motor on the motion platform, the control of light source, etc. FIG. 5 is a block diagram of the internal functional modules of the FPGA.

The internal functional modules of FPGA include:
1) USB interface control module: FPGA internal USB firmware program, implements communication between the FPGA unit and the USB interface of the upper computer.
2) clock module: carries out frequency division and multiplication processes on an external 12 MHz clock, and generates clock signals of various frequencies required by the operation of the FPGA unit.
3) command analysis module: analyzes command received from the upper computer, generates an executive order according to a stipulated command protocol, and sends the executive order to various modules for execution.
4) motor control module: executes 3-axis motor control command sent from the command analysis module, and carries out subdivision and variable speed control of the motor of each axis, and eventually implements 3-axis linkage control through transmission of different commands to the motor drive unit.
5) light source control module: controls 5 LED infrared light sources and 3 visual aid light sources of the optical system, the 3 visual aid light sources are used to guide the eye-glazing direction of a patient, and the 5 LED infrared light sources are used to aid in focusing.

The upper computer software of the control system of the automatic optometry analysis system for children is mainly responsible for the completion of tasks such as processing the collection of objective optometry data, retrieving and managing the expert database, completing the process of eyeglass prescriptions and transmitting the eyeglass prescriptions on the basis of pre-processing. Since the refractometer and the eyeglass prescription database are two separate devices, it is necessary to write special driver program and software in order to make those devices work properly.

a) Writing of Driver Program

A driver program can be written by some special tools for driver development, such as Driver Studio, WinDriver, etc. When carrying out development using Driver Studio 3.2, one should note that it is necessary to enter information in the USB Vendor ID and USB Product ID which are consistent with those described in the firmware device. Since PDIUSBD12 chip of Philips is used, the Vendor ID of the device is set as 0x0471. After the generation of a driver framework using Driver Wizard of Driver Studio, one can use Visual C++ 6.0 to carry out modification of the function of the project file generated by Driver Wizard according to one's need. Also, one can write a vendor-specific request and carry out processing of customized IO control interface function. After all these are completed, one can then compile the driver program. After successful compilation of the driver program, one can put it under the same category of the .inf file generated automatically by the Driver Studio. When searching for the driver, one can simply specify this category.

b) Writing of Application Program of Upper Computer

Since the device uses USB interface for communication between the upper computer and the device, the application program of the upper computer can achieve the access of the device through the USB driver. The writing of application program of the upper computer should comply with the interface specification defined by the USB driver. Generally speaking, after a driver project is generated by the Driver Wizard, an ioctl.h file is generated simultaneously. This file is a bridge established between the application program and the driver. It defines the interface of the driver program. One needs to apply it when writing the application program.

The entire application program of the upper computer can be divided into 6 regions, including video display region, (direct control) operation region, MOTOR (motor) control region, LED control region, real-time processing (data) display region, and status feedback data display region. The function of human-computer interaction of the system can be designed and completed using VC++6.0 compilation environment on windows platform. One can visually display tracking and focusing processes, and carry out easily-controlled visualized process of controlling of human eye tracking. The human eye tracking system can be completely controlled through human-computer interface.

The application program of the upper computer may be based on the database of children ophthalmologists. It uses database building language and C language to carry out statistics and analysis of successful eyeglass prescription cases of experts, develop database model with great coverage, generate an optometry database of 3~18 years old patients for enquiring and indexing through human-computer interface.

The automatic optometry analysis system for children of the present application may involve study of successful optometric cases of children, including management (update, enquiry, storage, indexing, etc.) of framework and optometry database of children ophthalmologists, and solving of unusual data access and trend management. It can carry out technical modification of existing refractometers, and involves development of operation mode, interface expansion, communication driver, and control software.

Apart from the main function of general optometry, children optometry correcting equipment of the present application adds a special corrective function of optometry for patients under 18 years of age. It has fully considered the effect and requirement of the potential of vision development as well as regulation and relaxation mechanism of children on eyeglass prescription. It pertinently provides a personalized eyeglass prescription according to the vision development pattern of children. Its successful development and usage can satisfy effective corrective treatment for children with ametropia. It will benefit hundreds of millions of children. Its wide spread application is of great significant. It is an important topic that worth exploring by children ophthalmology practitioners. Application and promotion of the system has a very promising prospect.

FIGS. 6-9 show the conversion formula and examples of ametropia of the automatic optometry analysis system for children according to an embodiment of the present application. The eyeglass prescription conversion formula is as follows:

spherical lens power of eyeglass prescription=spherical lens power after pupillary dilation−f1 coefficient cylindrical lens power of eyeglass prescription=cylindrical lens power after pupillary dilation−f2 coefficient axis value of eyeglass prescription=axis value after pupillary dilation.

(Note: wherein f1 coefficient and f2 coefficient possess age correlation and correlation of power after pupillary dilation)

6-year-old patient, anteroposterior eye position

1. Nearsightedness

|  | OD | OS |
|---|---|---|
| Power before pupillary dilation | −5.00 DS = −1.25 DC × 150 | −4.75 DS = −1.50 DC × 150 |
| Power after pupillary dilation | −2.00 DS = −1.00 DC × 150 | −3.25 DS = −1.00 DC × 150 |
| Eyeglass prescription 1 | −1.50 DS = −0.75 DC × 150 | −2.50 DS = −0.75 DC × 150 |
| Eyeglass prescription 2 | −1.75 DS = −0.50 DC × 150 | −2.75 DS = −0.75 DC × 150 |

2. Farsightedness

|  | OD | OS |
|---|---|---|
| Power after pupillary dilation | +5.00 DS = +1.50 DC × 150 | +5.25 DS = +1.75 DC × 150 |
| Power before pupillary dilation | +2.00 DS = +1.25 DC × 150 | +2.75 DS = +1.50 DC × 150 |
| Eyeglass prescription 1 | +2.75 DS = +1.00 DC × 150 | +3.00 DS = +1.25 DC × 153 |
| Eyeglass prescription 2 | +2.50 DS = −0.75 DC × 150 | +2.50 DS = +1.00 DC × 150 |

Farsightedness (symbol "+")

Normal Standard Eye Accommodation:

According to age groups, such as 1-3, 4-6, 7-9, 10-12, 13-15 and 16-18, distinguish the normal standard eye accommodation for each age group, and indicate by international standard vision chart, (e.g. 0.1 . . . 1.5).

In general, when children are at the age of 3, their eyes have an accommodation capability of about 300 degrees. As children grow older, accommodation capability decreases by about 25 degrees every year. At the age of 15, there is a decrease of 300 degrees in 12 years. According to the predetermined age groups, one can determine the accommodation degree for each age group. For example, the 1-3 age group can be set at 300 degrees. The 4-6 age group is a subtraction of predetermined degrees, e.g. 50-75, from the 1-3 age group, and so on such that one can determine the correction coefficient for each age group. When the power of myopia or hyperopia is determined, optometric data will be corrected by using the correction coefficient so that the actual power in the eyeglass prescription can be obtained.

Large pupil spherical lens-small pupil spherical lens=actual eye accommodation:

1. Both spherical lens and cylindrical lens can be null (display a blank), if the cylindrical lens is null, the axis is null (blank, i.e. axis is not required), astigmatic axis is marked by 1-180 (when there is no astigmatism, no astigmatism axis is required, i.e. axis is null).
2. in an eyeglass prescription result, spherical lens and cylindrical lens are positive numbers, minimum value is blank and is considered as zero.
3. large pupil spherical lens must be larger than small pupil spherical lens.
4. large pupil spherical lens is +0.25 DS to +15.00 DS; large pupil cylindrical lens is +0.25 DC to +8.25 DC.
5. one large pupil cylindrical lens may correspond to five small pupil cylindrical lenses.

Nearsightedness (symbol "−"):

1. Both spherical lens and cylindrical lens can be null (that is 0). If the cylindrical lens is null, axis does not exist. If large pupil spherical lens is null, its corresponding small pupil spherical lens power is larger than or equal to the absolute value of −0.25 DS.
2. absolute value of large pupil spherical lens power is absolutely smaller than absolute value of small pupil spherical lens power.
3. axis is a positive integer of 1-180 without decimal point (round up or down, round to a whole number).
4. large pupil spherical lens is −0.25 DS to −15.00 DS (incrementing in order by a unit of 0.25); large pupil cylindrical lens is −0.25 DC to −7.00 DC.
5. axis can be set as an input value, and large pupil, small pupil and eyeglass prescription axes can be consistent.

Specific embodiments have been described above with reference to the accompanying drawings. However, the present application is not limited to the above specific embodiments. The above specific embodiments are merely illustrative and should not be considered as limiting. It should be noted that, upon reading the above disclosure, a person skilled in the art can make various other changes or modifications without departing from the scope of the appended claims.

What is claimed is:

1. An automatic optometry analysis system for children, comprising a main control board for obtaining optometry data of a patient, and an upper computer connected with the main control board; wherein the upper computer carries out processing according to the optometry data obtained from the main control board, generates a corresponding preliminary eyeglass prescription data, corrects the preliminary eyeglass prescription data based on collected preset patient information, and generates a final eyeglass prescription suitable for the patient; wherein correction of the preliminary eyeglass prescription data based on the collected preset patient information comprises the use of age-related correction coefficient to correct the preliminary eyeglass prescription data; wherein the main control board uses a field-programmable gate array (FPGA) unit as a central processing core; wherein the FPGA unit is connected with a USB interface through a USB interface control unit and connected with the upper computer through the USB interface, and the FPGA unit is connected with an optical system through an IO interface and connected with a motion platform with a 3-axis motor through an optoelectronic isolator; and wherein the motion platform is further connected with a motor drive unit, and the FPGA unit and the motor drive unit are both connected with a level conversion unit.

2. The automatic optometry analysis system for children as claimed in claim 1, wherein the FPGA unit is an EP3C16Q240C8N chip, the motor drive unit is a SLA7042M driver chip for special use in a 2-phase motor, the level conversion unit is a 16-bit 3.3V-5V SN74ALVC164245 level conversion chip, and the USB interface control unit is a PDIUSBD12 chip.

3. The automatic optometry analysis system for children as claimed in claim 1, wherein the FPGA unit comprises:
a USB interface control module as a FPGA internal USB firmware program for implementing communication between the FPGA unit and the USB interface of the upper computer;
a clock module for carrying out frequency division and multiplication processes on an external clock, and generating clock signals of various frequencies required by operation of the FPGA unit;
a command analysis module for analyzing command received from the upper computer, generating an executive order according to a stipulated command protocol, and sending the executive order to a corresponding module for execution;
a motor control module for executing a 3-axis motor control command sent from the command analysis module, and carrying out subdivision and variable speed control of the motor of each axis, and eventually implementing 3-axis linkage control through transmission of different commands to the motor drive unit; and
a light source control module for controlling an LED infrared light source and a visual aid light source of the optical system, the visual aid light source being used to guide eye-glazing direction of the patient, and the LED infrared light source being used to aid in focusing.

4. The automatic optometry analysis system for children as claimed in claim 1, wherein, in the eyeglass prescription, spherical lens power=spherical lens power after pupillary dilation−f1 coefficient, wherein the f1 coefficient possesses age correlation and correlation of spherical lens after pupillary dilation; cylindrical lens power=cylindrical lens power after pupillary dilation−f2 coefficient, wherein the f2 coefficient possesses age correlation and correlation of cylindrical lens after pupillary dilation; and axis=axis after pupillary dilation.

5. The automatic optometry analysis system for children as claimed in claim 4, wherein the eyeglass prescription is generated based on an expert database on children optometry of children, wherein the expert database includes a huge volume of optometry data from youngsters and children aged 3-18 formed by carrying out statistical analysis of successful eyeglass prescription cases of experts using database building language and C language so as to establish an associated database model; and wherein the automatic optometry analysis system for children displays or prints out two sets of eyeglass prescription based on recognition of patients' age, small pupil power and large pupil power.

6. The automatic optometry analysis system for children as claimed in claim 5, wherein ages of patients are divided into a predetermined number of age groups, and a correction coefficient corresponds to each age group in the eyeglass prescription such that eyeglass prescription power given in the eyeglass prescription increases as the age group increases; wherein in the eyeglass prescription, refraction condition of the patient after pupillary dilation is set as a primary reference factor, and refraction condition of the patient before pupillary dilation is set as a secondary reference factor.

7. The automatic optometry analysis system for children as claimed in claim 6, wherein:
the refraction condition includes farsightedness, in an eyeglass prescription, both spherical lens and cylindrical lens can be null, if the cylindrical lens is null, axis is null, astigmatic axis is marked by 1-180;
in an eyeglass prescription result, spherical lens and cylindrical lens are positive numbers, minimum value is blank and is considered as zero; large pupil spherical lens must be larger than small pupil spherical lens; large pupil spherical lens is +0.25DS to +15.00DS, large pupil cylindrical lens is +0.25DC to +8.25DC; and one large pupil cylindrical lens corresponds to five small pupil cylindrical lenses.

8. The automatic optometry analysis system for children as claimed in claim 6, wherein the refraction condition includes nearsightedness, in an eyeglass prescription, both spherical lens and cylindrical lens can be null, if the cylindrical lens is null, axis does not exist; if large pupil spherical lens is null, its corresponding small pupil spherical lens power is larger than or equal to the absolute value of −0.25DS; absolute value of large pupil spherical lens power is absolutely smaller than absolute value of small pupil spherical lens power; axis is a positive integer from 1-180 without decimal point; large pupil spherical lens is −0.25DS to −15.00DS, incrementing in order by a unit of 0.25, large pupil cylindrical lens is −0.25DC to −7.00DC, axis is set as an input value; and large pupil, small pupil and eyeglass prescription axes are consistent.

9. The automatic optometry analysis system for children as claimed claim 1, wherein, in the eyeglass prescription, spherical lens power =spherical lens power after pupillary dilation −f1 coefficient, wherein the f1 coefficient possesses age correlation and correlation of spherical lens after pupillary dilation; cylindrical lens power =cylindrical lens power after pupillary dilation −f2 coefficient, wherein the f2 coefficient possesses age correlation and correlation of cylindrical lens after pupillary dilation; and axis =axis after pupillary dilation.

10. The automatic optometry analysis system for children as claimed in claim 9, wherein the eyeglass prescription is generated based on an expert database on children optometry of children, wherein the expert database includes a huge volume of optometry data from youngsters and children aged 3-18 formed by carrying out statistical analysis of successful eyeglass prescription cases of experts using database building language and C language so as to establish an associated database model; and wherein the automatic optometry analysis system for children displays or prints out two sets of eyeglass prescription based on recognition of patients' age, small pupil power and large pupil power.

11. The automatic optometry analysis system for children as claimed in claim 10, wherein ages of patients are divided into a predetermined number of age groups, and a correction coefficient corresponds to each age group in the eyeglass prescription such that eyeglass prescription power given in the eyeglass prescription increases as the age group increases; wherein in the eyeglass prescription, refraction condition of the patient after pupillary dilation is set as a primary reference factor, and refraction condition of the patient before pupillary dilation is set as a secondary reference factor.

12. The automatic optometry analysis system for children as claimed in claim 11, wherein:

the refraction condition includes farsightedness, in an eyeglass prescription, both spherical lens and cylindrical lens can be null, if the cylindrical lens is null, axis is null, astigmatic axis is marked by 1-180;

in an eyeglass prescription result, spherical lens and cylindrical lens are positive numbers, minimum value is blank and is considered as zero; large pupil spherical lens must be larger than small pupil spherical lens; large pupil spherical lens is +0.25DS to +15.00DS, large pupil cylindrical lens is +0.25DC to +8.25DC; and one large pupil cylindrical lens corresponds to five small pupil cylindrical lenses.

13. The automatic optometry analysis system for children as claimed in claim 11, wherein the refraction condition includes nearsightedness, in an eyeglass prescription, both spherical lens and cylindrical lens can be null, if the cylindrical lens is null, axis does not exist; if large pupil spherical lens is null, its corresponding small pupil spherical lens power is larger than or equal to the absolute value of −0.25DS; absolute value of large pupil spherical lens power is absolutely smaller than absolute value of small pupil spherical lens power; axis is a positive integer from 1-180 without decimal point; large pupil spherical lens is −0.25DS to −15.00DS, incrementing in order by a unit of 0.25, large pupil cylindrical lens is −0.25DC to −7.00DC, axis is set as an input value; and large pupil, small pupil and eyeglass prescription axes are consistent.

14. The automatic optometry analysis system for children as claimed in claim 2, wherein, in the eyeglass prescription, spherical lens power =spherical lens power after pupillary dilation −f1 coefficient, wherein the f1 coefficient possesses age correlation and correlation of spherical lens after pupillary dilation; cylindrical lens power =cylindrical lens power after pupillary dilation −f2 coefficient, wherein the f2 coefficient possesses age correlation and correlation of cylindrical lens after pupillary dilation; and axis =axis after pupillary dilation.

15. The automatic optometry analysis system for children as claimed in claim 14, wherein the eyeglass prescription is generated based on an expert database on children optometry of children, wherein the expert database includes a huge volume of optometry data from youngsters and children aged 3-18 formed by carrying out statistical analysis of successful eyeglass prescription cases of experts using database building language and C language so as to establish an associated database model; and wherein the automatic optometry analysis system for children displays or prints out two sets of eyeglass prescription based on recognition of patients' age, small pupil power and large pupil power.

16. The automatic optometry analysis system for children as claimed in claim 15, wherein ages of patients are divided into a predetermined number of age groups, and a correction coefficient corresponds to each age group in the eyeglass prescription such that eyeglass prescription power given in the eyeglass prescription increases as the age group increases; wherein in the eyeglass prescription, refraction condition of the patient after pupillary dilation is set as a primary reference factor, and refraction condition of the patient before pupillary dilation is set as a secondary reference factor.

17. The automatic optometry analysis system for children as claimed in claim 16, wherein:

the refraction condition includes farsightedness, in an eyeglass prescription, both spherical lens and cylindrical lens can be null, if the cylindrical lens is null, axis is null, astigmatic axis is marked by 1-180;

in an eyeglass prescription result, spherical lens and cylindrical lens are positive numbers, minimum value is blank and is considered as zero; large pupil spherical lens must be larger than small pupil spherical lens; large pupil spherical lens is +0.25DS to +15.00DS, large pupil cylindrical lens is +0.25DC to +8.25DC; and one large pupil cylindrical lens corresponds to five small pupil cylindrical lenses.

18. The automatic optometry analysis system for children as claimed in claim 16, wherein the refraction condition includes nearsightedness, in an eyeglass prescription, both spherical lens and cylindrical lens can be null, if the cylindrical lens is null, axis does not exist; if large pupil spherical lens is null, its corresponding small pupil spherical lens power is larger than or equal to the absolute value of −0.25DS; absolute value of large pupil spherical lens power is absolutely smaller than absolute value of small pupil spherical lens power; axis is a positive integer from 1-180 without decimal point; large pupil spherical lens is −0.25DS to −15.00DS, incrementing in order by a unit of 0.25, large pupil cylindrical lens is −0.25DC to 7.00DC, axis is set as an input value; and large pupil, small pupil and eyeglass prescription axes are consistent.

* * * * *